(12) United States Patent
Odanaka (10) Patent No.: US 6,324,742 B1
(45) Date of Patent: Dec. 4, 2001

(54) METHOD OF UNITING OPTICAL FIBERS (75) Inventor: Kunio Odanaka, Tokyo (JP)

(73) Assignee: Machida Endoscope Co., Ltd., Tokyo (JP)

(*) Notice: Subject to any disclaimer, the term of this patent is extended or adjusted under 35 U.S.C. 154(b) by 0 days.

(21) Appl. No.: 09/568,042

(22) Filed: May 10, 2000

Related U.S. Application Data (62) Division of application No. 08/043,743, filed on Apr. 7, 1993, now Pat. No. 6,101,703.

(30) Foreign Application Priority Data

Apr. 15, 1992 (JP) .................................................. 4-121285

(51) Int. Cl.⁷ .................................................. B23P 11/02
(52) U.S. Cl. .................................. 29/447; 29/516; 385/55
(58) Field of Search .......................... 29/447, 515, 516, 29/517; 385/54, 55, 99, 102

(56) References Cited

U.S. PATENT DOCUMENTS

| | | | |
|---|---|---|---|
| 3,579,805 | * 5/1971 | Kast | 29/447 X |
| 3,580,775 | * 5/1971 | Siegmund | 385/117 X |
| 3,834,008 | * 9/1974 | Witt et al. | 29/447 |
| 3,914,015 | 10/1975 | McCartney . | |
| 4,198,081 | * 4/1980 | Harrison et al. | 29/447 X |
| 4,352,542 | * 10/1982 | Tydings | 385/70 |
| 4,597,632 | * 7/1986 | Mallison | 385/72 |
| 4,631,796 | * 12/1986 | Inomata et al. | 29/447 |
| 4,743,084 | * 5/1988 | Manning | 385/84 |
| 4,894,906 | * 1/1990 | Huang | 29/599 |
| 4,921,323 | * 5/1990 | Delahanty et al. | 385/96 |
| 5,150,516 | * 9/1992 | Boero et al. | 29/469.5 X |
| 5,231,681 | * 7/1993 | Bergqvist | 385/32 |

FOREIGN PATENT DOCUMENTS

| | | | |
|---|---|---|---|
| A-2 025 084 | 6/1978 | (EP) . | |
| 2053766 | * 2/1981 | (GB) | 29/469.5 |
| 2185923 | * 8/1987 | (GB) | 29/447 |
| 59-34239 | 2/1984 | (JP) . | |
| 59-43903 | 3/1984 | (JP) . | |
| 0121006 | * 7/1984 | (JP) | 385/117 |
| 64-59304 | 3/1989 | (JP) . | |
| 1-109310 | 4/1989 | (JP) . | |

OTHER PUBLICATIONS

"KSM Alloy", published by Kanto Tokushuko K.K., date unknown.
European Search Report dated Jun. 14, 1994.

* cited by examiner

Primary Examiner—David P. Bryant
(74) Attorney, Agent, or Firm—Fish & Richardson P.C.

(57) ABSTRACT

After a number of optical fibers are inserted into a tubular member of a shape memory alloy, the tubular member is returned to its memorized shape by heating to reduce a cross-sectional area of a reception space of the tubular member, thereby uniting the optical fibers received in the tubular member. In a modified form of the invention, a number of optical fibers are inserted into a reception space between two tubular members at least one of which is made of a shape memory alloy, and then the one tubular member is heated to be returned to its memorized shape to reduce a cross-sectional area of the reception space between the two tubular members, thereby uniting the optical fibers. In another modified form of the invention, a number of optical fibers are inserted into a reception space formed between an inner periphery of a tubular member and a partition plate of a shape memory alloy, and then the partition plate is heated to be returned to its memorized shape to reduce a cross-sectional area of the reception space, thereby uniting the optical fibers.

1 Claim, 9 Drawing Sheets

ND OF UNITING OPTICAL FIBERS

This application is a div. of Ser. No. 08/043,743 filed Apr. 7, 1993, U.S. Pat. No. 6,101,703.

BACKGROUND OF THE INVENTION

This invention relates to a method of uniting a number of optical fibers into a bundle.

An optical fiber bundle has been widely used for transmitting illumination light in an endoscope. The optical fiber bundle is obtained by uniting or joining at least opposites ends of a number of optical fibers. Generally, tubular members have conventionally been used for this uniting operation. More specifically, the end portions of a number of optical fibers to which an adhesive has been applied are inserted into the tubular members, and the optical fibers are united together upon solidification of the adhesive. It is preferred that as many optical fibers as possible be inserted into the tubular member so as to increase the density of filling of the optical fibers. In the above method, however, when trying to insert as many optical fibers as possible into the tubular member, the optical fibers are rubbed by the inner surface of the tubular member, and are damaged. Therefore, to increase the density of filling of the optical fibers has been limited.

Japanese Laid-Open Utility Model Application No. 59-43903 discloses a method of uniting optical fibers together, in which a number of optical fibers are first inserted into a tubular member of a circular cross-section, and then a wedge member is inserted into the tubular member, thereby increasing the density of filling of the optical fibers. However, when the wedge member is inserted into the tubular member, the wedge member rubs the optical fibers, and therefore may damage them.

In some cases, optical fibers in a bent condition are united together. For example, Japanese Laid-Open Patent Application No. 59-34239 shows in FIG. 5 a front end structure of an endoscope of a side-viewing type. End portions of optical fibers are bent generally right-angularly or perpendicularly, and in this condition they are united together by a uniting member. Although not described in detail in this publication, this uniting member is composed of two halves, and a pair of curved grooves are formed respectively in opposed surfaces of the two halves. The optical fibers are received in these grooves, and the two halves are connected together, with the two grooves mated together, thereby uniting the optical fibers. In this uniting method, the density of filling of the optical fiber is low, and the uniting operation is quite cumbersome.

A pamphlet "KSM alloy", published by Kanto Tokushuko K. K, discloses a joint for connecting two pipes together. This joint has a tubular shape, and is made of a shape memory alloy. Opposed ends of the two pipes are inserted respectively into the opposite end portions of the joint, and then heat is applied to the joint to return it to its memorized configuration, that is, a smaller diameter, thereby connecting the two pipes together.

SUMMARY OF THE INVENTION

It is an object of this invention to provide a method of uniting optical fibers with a high filling density without damaging the optical fibers.

According to one aspect of the present invention, there is provided a method of uniting a number of optical fibers comprising the steps of:

(a) processing a tubular member of a shape memory alloy with a reception space in such a manner that the cross-sectional area of the reception space is larger than that in a memorized shape of the tubular member;

(b) inserting a number of optical fibers into the tubular member; and (c) subsequently heating the tubular member to return the same to its memorized shape to reduce the cross-sectional area of the reception space, thereby uniting the optical fibers received in the tubular member.

According to another aspect of the invention, there is provided a method of uniting a number of optical fibers comprising the steps of:

(a) inserting an inner tubular member and a number of optical fibers into an outer tubular member, the outer and inner tubular members forming a reception space therebetween in which the optical fibers are received, and at least one of the outer and inner tubular member being made of a shape memory alloy; and (b) subsequently heating the one tubular member to return the same into its memorized shape to reduce a cross-sectional area of the reception space, thereby uniting the optical fibers received in the reception space.

According to a further aspect of the invention, there is provided a method of uniting a number of optical fibers comprising the steps of:

(a) inserting a partition plate and a number of optical fibers into a tubular member, so that an internal space of the tubular member is divided into two sections, one of the two sections serving as a reception space for receiving the optical fibers, and the partition plate being made of a shape memory alloy; and (b) subsequently heating the partition plate to return the same to its memorized shape to reduce a cross-sectional area of the reception space, thereby uniting the optical fibers received in the reception space.

DESCRIPTION OF THE PREFERRED EMBODIMENTS

Figure 1:
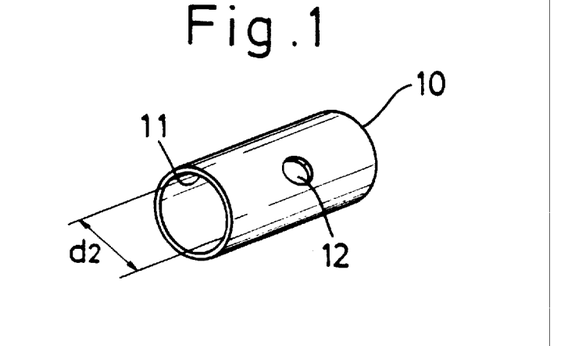
FIG. 1 is a perspective view of a tubular member of a shape memory alloy expanded in diameter.
Figure 2:
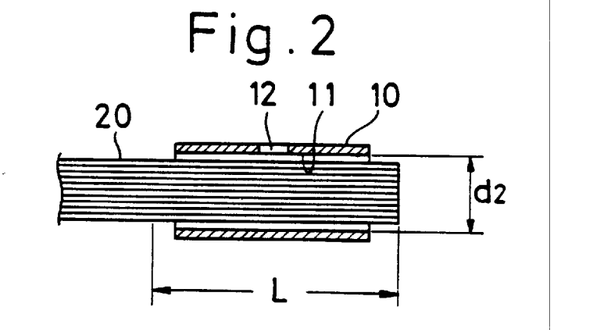
FIG. 2 is a longitudinal cross-sectional view of the tubular member into which end portions of a number of optical fibers are inserted.
Figure 3:
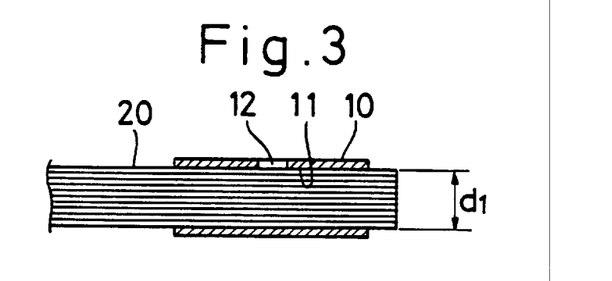
FIG. 3 is a longitudinal cross-sectional view, showing a condition in which the tubular member of FIG. 2 is reduced in diameter by heating, thereby uniting the optical fibers together.
Figure 4:
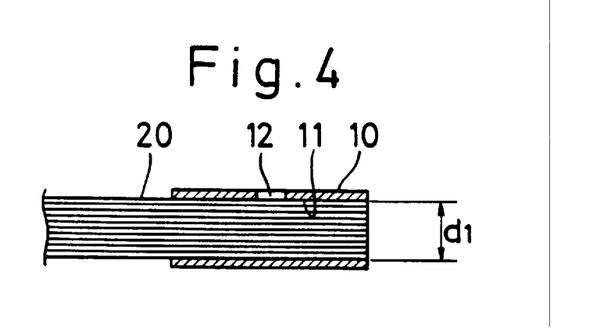
FIG. 4 is a longitudinal cross-sectional view, showing a condition in which the end portions of the united optical fibers of FIG. 3 are cut off.

Methods of the present invention will now be described with reference to the drawings. First, a first embodiment of the invention will be described with reference to FIGS. 1 to 4. As shown in FIG. 1, a tubular member 10 is prepared. This tubular member 10 is made of a shape memory alloy. The tubular member 10 is processed with respect to its memory at a temperature higher than an ordinary temperature (room temperature), and its memorized shape is a cylinder having an inner diameter $d_1$, as shown in FIGS. 3 and 4. The tubular member 10 is expanded in diameter at the ordinary temperature into a cylinder having an inner diameter $d_2 (d_2 > d_1)$, as shown in FIGS. 1 and 2. The internal space or interior of the tubular member 10 serves as a reception space 11. The cross-sectional area of the reception space 11 is uniform throughout the length of the tubular member 10. A through hole 12 is formed through the peripheral wall of the tubular member 10.

On the other hand, as shown in FIG. 2, there are prepared a maximum number (for example, several thousands to several tens of thousands) of optical fibers 20 which can be inserted into the tubular member 10, having the inner diameter $d_2$, without damage. One ends of these optical fibers 20 are disposed generally in a common plane, and in this condition an adhesive is applied to almost all of the optical fibers 20 over a predetermined distance (indicated by L in FIG. 2) from the one ends thereof.

Then, as shown in FIG. 2, a number of optical fibers 20 mentioned above are inserted into the reception space 11 of the tubular member 10, and one ends of the optical fibers 20 are projected from one end of the tubular member 10. Since the diameter of the tubular member 10 is large, the optical fibers 20 can be easily inserted into the tubular member 10 without damage. The tubular member 10 is disposed on those portions of the optical fibers 20 to which the adhesive has been applied.

Then, as shown in FIG. 3, the tubular member 10 is heated to be returned to its memorized shape, that is, into the cylindrical shape having the inner diameter $d_1$. As a result, the optical fibers 20 are united together by the tubular member 10. Thus, even though the inner diameter $d_1$ of the tubular member 10 is small, the number of optical fibers 20 to be united together can be increased, so that the density of filling of the optical fibers 20 can be increased.

The adhesive is cured or set by the above heating. The cured adhesive prevents the optical fibers 20 from being withdrawn from the tubular member 10 after the optical fibers 20 are united together. The adhesive fills in gaps between the optical fibers 20 to thereby prevent the intrusion of water.

When the tubular member 10 is reduced or contracted in diameter by heating, the adhesive leaks from the through hole 12 in the tubular member 10. Therefore, the amount of flow of the adhesive along the optical fibers 20 can be reduced. As a result, straight portions of the optical fibers 20 which are unable to be bent after the curing of the adhesive can be shortened.

Then, as shown In FIG. 4, the end portions of the united optical fibers 20 projected from the end of the tubular member 10 are cut off, so that the cut ends of the optical fibers 20 lie substantially flush with the end of the tubular member 10. Then, the end faces of the optical fibers 20 are polished. The other ends of the optical fibers 20 are united together by the use of another tubular member 10' similar to the tubular member 10 in a manner described above. An optical fiber bundle 25, obtained by uniting both ends of the optical fibers by the respective tubular members 10 and 10', is incorporated, for example, into an endoscope 50 (FIG. 5) for transmitting illumination light.

Figure 5:
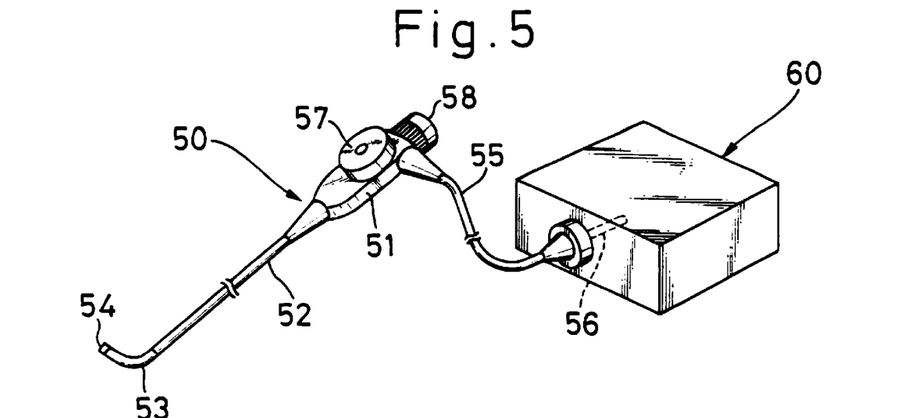
FIG. 5 is a perspective view, showing an endoscope, incorporating the optical fibers united at their opposite ends, and a light source device.

The endoscope 50 comprises a body 51, a flexible insertion portion 52 extending from the body 51, a bending portion 53 extending from a front end of the insertion portion 52, a rigid tip member 54 provided at a front end of the bending portion 53, a light guide cable 55 extending from the body 51, and a connector 56 mounted on a distal end of the light guide cable 55. A manipulation member 57 is mounted on the body 51, and by operating this manipulation member 57, the bending portion 53 is bent in a remotely-controlled manner. An ocular portion 58 is further provided on the body 51.

Figure 6:
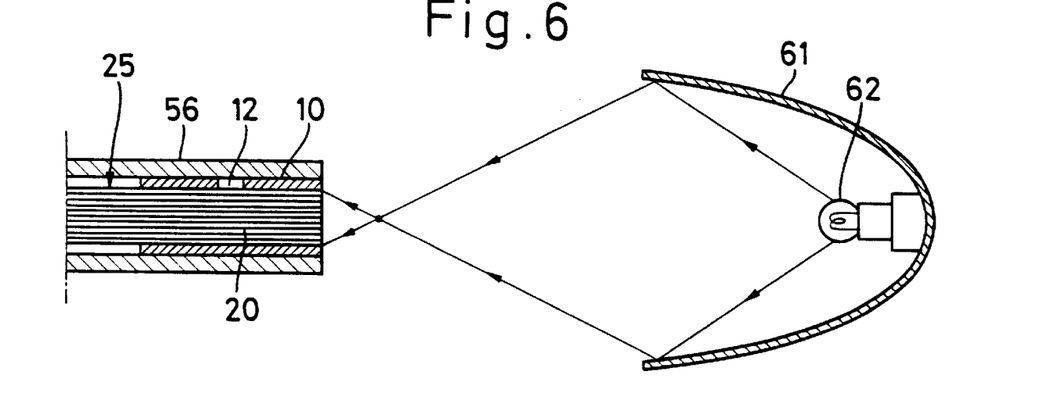
FIG. 6 is a vertical cross-sectional view showing the relation between a connector of the endoscope containing one end portions of the united optical fibers and a light source.
Figure 7:
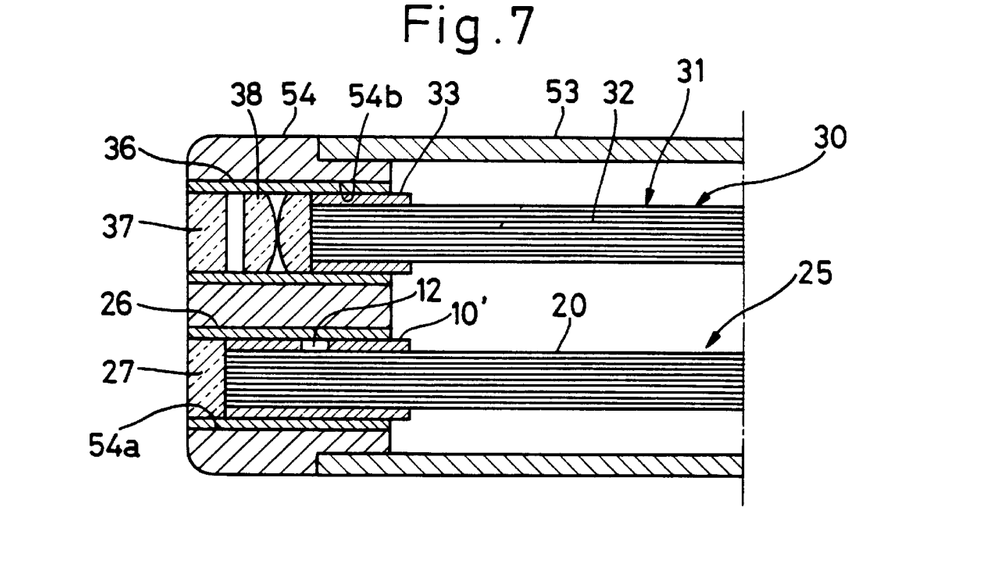
FIG. 7 is a longitudinal cross-sectional view of a tip member of the endoscope containing the other end portions of the united optical fibers.

As shown in FIG. 6, one end portion of the optical fiber bundle 25 inserted into the connector 56 of a tubular shape, and is fixed to this connector 56 by a screw (not shown) which is threaded through the peripheral wall of the connector 56, and is firmly held at its distal end against the outer peripheral surface of the tubular member 10. The optical fiber bundle 25 passes sequentially through the light guide cable 55, the body 51, the insertion portion 52 and the bending portion 53, and is inserted into and fixed to the tip member 54 at the other end portion thereof, as shown in FIG. 7. More specifically, the tubular member 10' of the optical fiber bundle 25 is inserted into and fixed to a retainer tube 26. A flat pane 27 of glass, serving as an illumination window, is fitted in the front end of the retainer tube 26. The retainer tube 26 is fitted in and fixed to a through hole 54a formed through the tip member 54.

An image transmission optical system 30 shown in FIG. 7 is provided between the ocular portion 58 and the tip member 54. The image transmission optical system 30 comprises an optical fiber bundle 31. The optical fiber bundle 31 comprises a number of optical fibers 32 united at their opposite ends by tubular members 33. One end portion of the optical fiber bundle 31, as well as a flat pane 37 of glass (which serves as an inspection window) and an objective lens 38, is fitted in and fixed to a retainer tube 36. This retainer tube 36 is inserted into and fixed to a through hole 54b of the tip member 54. The other end portion of the optical fiber bundle 31 is fixed, together with an ocular lens, to the ocular portion 58.

As shown in FIGS. 5 and 6, the connector 56 of the endoscope 50 is connected to a light source device 60. The light source device 60 comprises a concave mirror 61 within a housing, and a lamp 62 which serves as a light source and mounted on the concave mirror 61. Illumination light from the lamp 62 is reflected by the concave mirror 61 to converge, and is incident on one end faces of the optical fibers 20 supported by the connector 56. This incident light passes through the optical fibers 20, and is applied to a body cavity via the illumination window 27. An image of an inner wall of the body cavity can be observed from the ocular portion 58 via the image transmission optical system 30.

In the connector 56, since the density of filling of the optical fibers 20 in the tubular member 10 is high, the connector 56 can efficiently receive the illumination light from the lamp 62. Also, in the tip member 54, since the density of filling of the optical fibers 20 in the tubular member 10' is high, a large amount of light can be applied from the tubular member 10' having a relatively small transverse cross-sectional area.

Other embodiments of the present invention will be described below. In these embodiments, those portions corresponding respectively to those of preceding embodiments are designated by identical reference numerals, respectively, and detailed explanation thereof will be omitted. In all of the embodiments described hereinafter, an adhesive is used for uniting optical fibers together.

Figure 8:
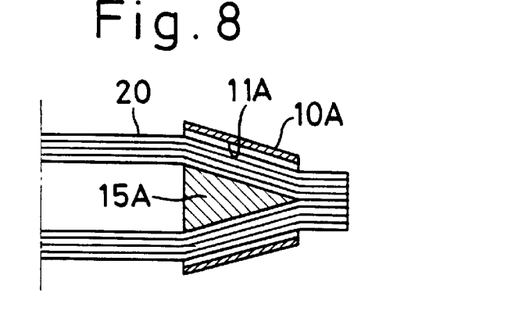
FIG. 8 is a longitudinal cross-sectional view, showing a tubular member which is used in a modified optical fiber uniting method and has not yet been heated.
Figure 9:
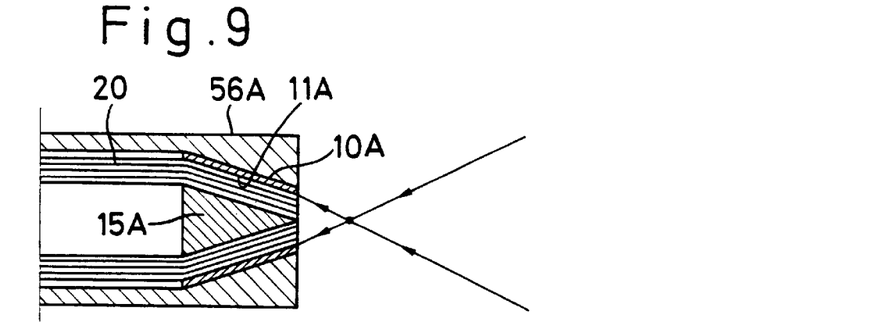
FIG. 9 is a longitudinal cross-sectional view of a connector containing one end portions of optical fibers united together by the method of FIG. 8.

In the embodiment shown in FIGS. 8 and 9, a tubular member 10A is uniform in thickness throughout the length thereof, and an inner diameter of the tubular member 10A, as well as its outer diameter, is decreasing progressively toward one end of the tubular member 10A. A reception space 11A of the tubular member 10A has a circular transverse cross-section, and is decreasing progressively toward one end thereof. The tubular member 10A is made of a shape memory alloy, and is processed in such a manner that it is larger in diameter than its memorized shape. As shown in FIG. 8, optical fibers 20 are inserted into the reception space 11A of the tubular member 10A, and then a core 15A of a conical shape is inserted into a bundle of optical fibers 20. As a result, the optical fibers are disposed between the outer peripheral surface of the core 15A and the inner peripheral surface of the tubular member 10A. In the condition shown in FIG. 8, the tubular member 10A is heated to be returned to its memorized shape having the smaller diameter, so that the optical fibers 20 are united together. Thereafter, the end portions of the optical fibers 20 projected from one end of the tubular member 10A is cut off, so that the cut ends of the optical fibers 20 lie substantially flush with the one end of the tubular member 10A. As shown in FIG. 9, the end portions of the thus united optical fibers 20 are inserted into and fixed to a connector 56A of an endoscope. The end portions of the optical fibers 20 flare to the left in FIG. 9, and therefore the angle between illumination light, which is emitted from a light source to be incident on each optical fiber 20, and the optical fiber 20 is small, so that the optical fibers 20 can efficiently receive the illumination light.

Figure 10:
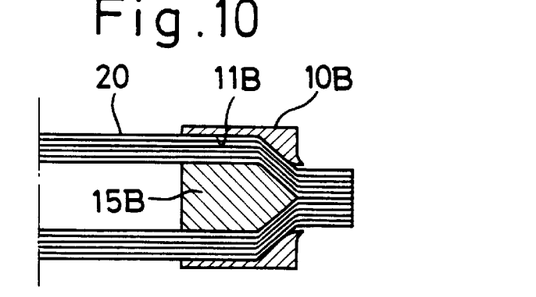
FIG. 10 is a longitudinal cross-sectional view, showing a tubular member which is used in another modified optical fiber uniting method and has not yet been heated.
Figure 11:
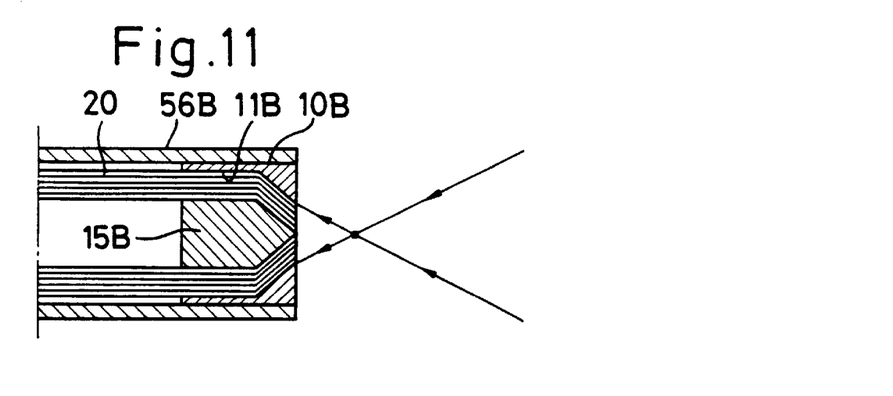
FIG. 11 is a longitudinal cross-sectional view of a connector containing one end portions of optical fibers united together by the method of FIG. 10.
Figures 12, 13, 14:
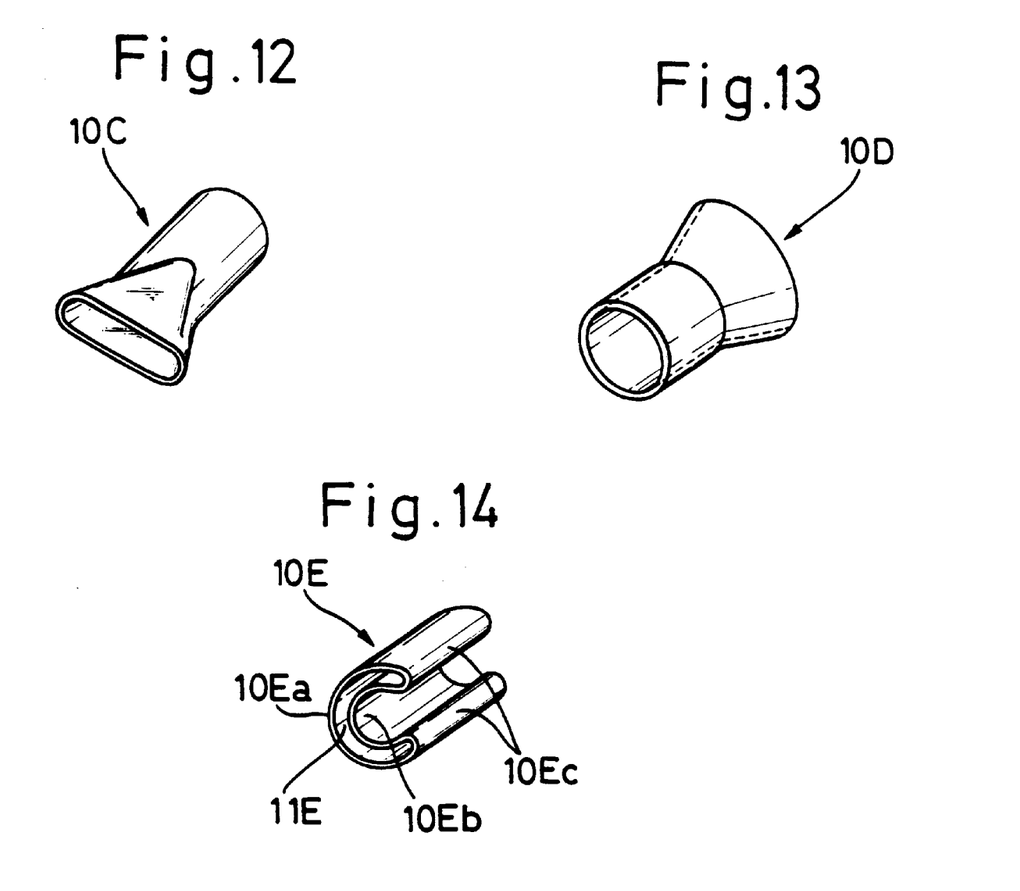
FIGS. 12 to 16 are perspective views respectively showing modified tubular members of various shapes used for uniting optical fibers.
Figure 15:
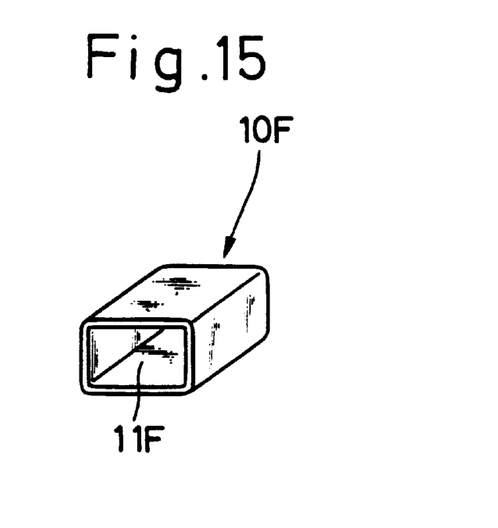
Figure 16:
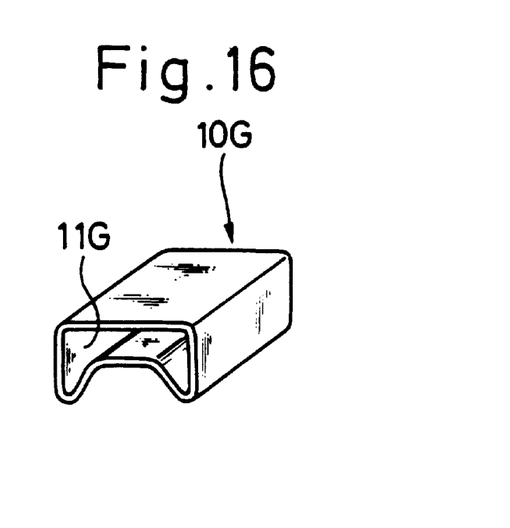

In the embodiment shown in FIGS. 10 and 11, a tubular member 10B made of a shape memory alloy has a cylindrical outer peripheral surface. A reception space 11B of the tubular member 10B has a circular transverse cross-section, and is decreasing at its one end portion progressively toward one open end of the tubular member 10B. The tubular member 10B is processed in such a manner that this open end is larger in diameter than its memorized shape. A core 15B has a left end portion of a cylindrical shape, and a right end portion of a conical shape. As shown in FIG. 10, optical fibers 20 are disposed between the tubular member 10B and the core 15B. When the tubular member 10B is heated, the open end of the tubular member 10B is returned to its memorized shape as shown in FIG. 11, so that the optical fibers 20 are united together. The end portions of the thus united optical fibers 20 are inserted into and fixed to a connector 56B.

FIGS. 12 to 16 respectively show modified tubular members of a shape memory alloy in their respective memorized shapes, which tubular members are used for uniting optical fibers. The tubular member 10C of FIG. 12 has one end portion of a circular transverse cross-section, and the other end portion of an oval transverse cross-section. The tubular member 10D of FIG. 13 has a cylindrical shape at its one end portion, and is increasing in diameter toward the other end. Each of the tubular members 10C and 10D are processed in such a manner that it is larger in diameter than its memorized shape throughout the length thereof. The tubular member 10E of FIG. 14 includes an outer arcuate portion 10Ea, an inner arcuate portion 10Eb, and a pair of connecting portions 10Ec interconnecting the outer and inner arcuate portions 10Ea and 10Eb at opposite ends thereof. A reception space 11E of the tubular member 10E has a generally C-shape. The tubular member 10E is processed in such a manner that the outer arcuate portion 10Ea is larger in diameter than its memorized shape. The tubular member 10F of FIG. 15, as well as the tubular member 10G of FIG. 16, has a generally rectangular cross-section. Each of these tubular members 10F and 10G is processed in such a manner that its reception space 11F, 11G is larger in cross-sectional area than that of the memorized shape.

Figure 17:
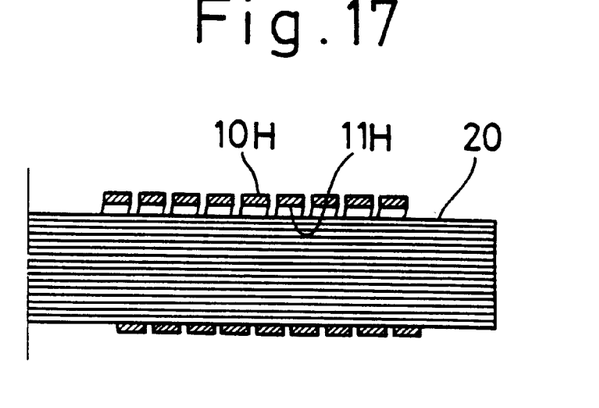
FIG. 17 is a longitudinal cross-sectional view, showing a tubular member which is used in a further modified optical fiber uniting method and has not yet been heated.
Figure 18:
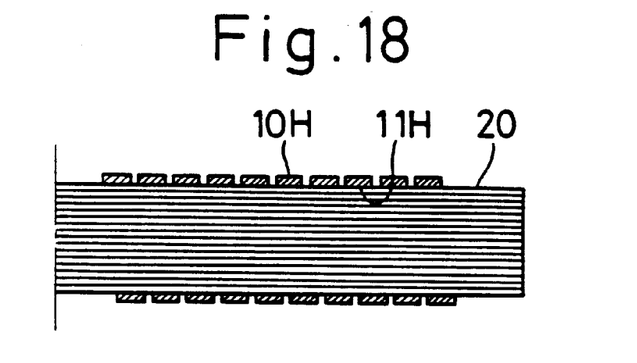
FIG. 18 is a longitudinal cross-sectional view showing a condition in which the tubular member of FIG. 17 is reduced in diameter by heating to unit optical fibers.
Figure 19:
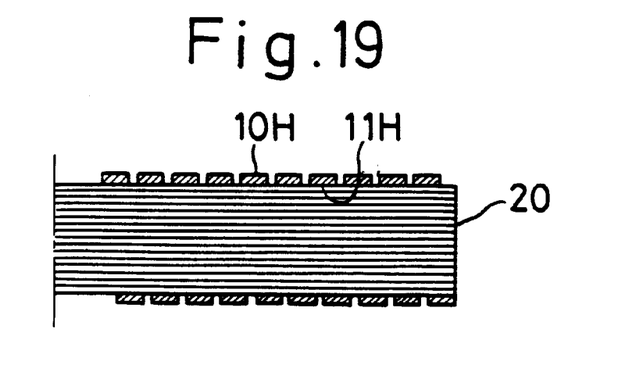
FIG. 19 is a longitudinal cross-sectional view showing a condition in which the end portions of the united optical fibers of FIG. 18 are cut off.

In the embodiment shown in FIGS. 17 to 19, a coil 10H made of a shape memory alloy is used as a tubular member. As shown in FIG. 17, the coil 10H is processed in such a manner that it is larger in diameter than its memorized shape. A number of optical fibers 20 are inserted into a reception space 11H of the tubular member 10H, and one end portions of the optical fibers 20 are projected from one end of the tubular member 10H. Then, as shown in FIG. 18, the tubular member 10H is heated to be returned to its memorized shape having the smaller diameter, thereby uniting the optical fibers 20 together. Then, as shown in FIG. 19, the end portions of the optical fibers 20 projected from the tubular member 10H are cut off, so that the cut ends of the optical fibers 20 lie substantially flush with the end of the tubular member 10. Then, the end faces of the optical fibers 20 are polished.

The optical fibers united by the above tubular members 10C to 10H are used for transmitting illumination light in an endoscope.

Figure 20:
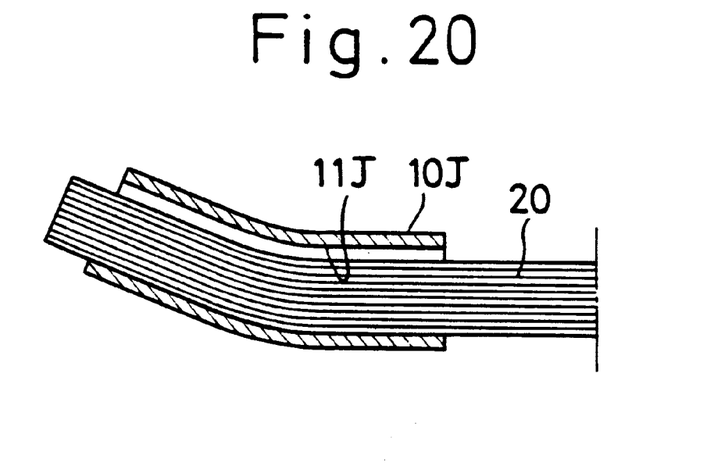
FIG. 20 is a longitudinal cross-sectional view, showing a tubular member which is used in a further modified optical fiber uniting method and has not yet been heated.
Figure 21:
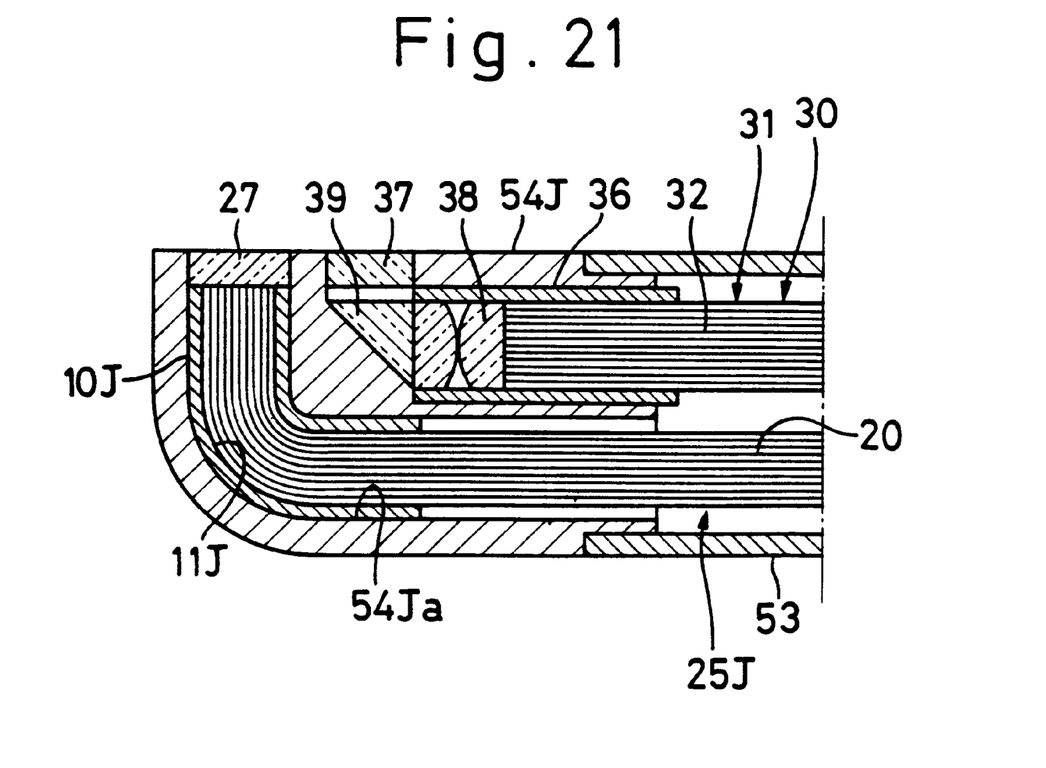
FIG. 21 is a longitudinal cross-sectional view, showing a tip member containing end portions of optical fibers united by the method of FIG. 20.

The embodiment shown in FIGS. 20 and 21 is directed to a method of obtaining an optical fiber bundle 25J used in an endoscope of a side-viewing type. As shown in FIG. 21, in its memorized shape, a tubular member 10J used in this embodiment has a circular cross-section, and has an axis of an L-shape which is bent generally perpendicularly. As shown in FIG. 20, the tubular member 10J is processed in such a manner that it is larger in diameter and is curved along its axis more gently than its memorized shape. One end portions of a number of optical fibers 20 are inserted into the tubular member 10J. At this time, the curvature or bending of the tubular member 10J in the axial direction is gentle, and besides the cross-sectional area of a reception space 11J is large, and therefore the insertion of the optical fibers 20 is easy. Then, the tubular member 10J is heated to be returned to its memorized shape, so that the tubular member 10J is reduced in diameter and is brought into the perpendicularly-bent condition, thereby uniting the one end portions of the optical fibers 20. Then, the end portions projected from the tubular member 10J are cut off. The other end portions of the optical fibers 20 are united together in the manner as described in any one of the above embodiments.

As shown in FIG. 21, one end portion of the thus obtained optical fiber bundle 25J is incorporated into a tip member 54J of the endoscope. The tip member 54J is composed of two halves having L-shaped grooves in their opposed surfaces, respectively. The two halves are joined together with the tubular member 10J fitted in the opposed L-shaped grooves, thereby attaching the optical fiber bundle 25J to the tip member 54J. The pair of grooves cooperate with each other to form a through hole 54Ja receiving the tubular member 10J. One end portion of an image transmission optical system 30 is also attached to the tip member 54J when the above two halves are joined together. A prism 39 is provided between an inspection window 37 and an objective lens 38.

Figure 22:
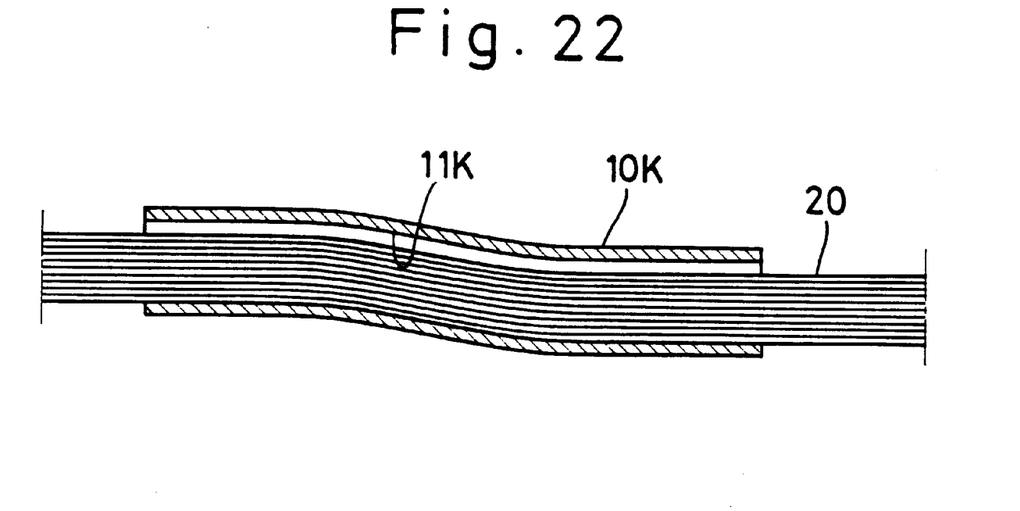
FIG. 22 is a longitudinal cross-sectional view, showing a tubular member which is used in a further modified optical fiber uniting method and has not yet been heated.
Figure 23:
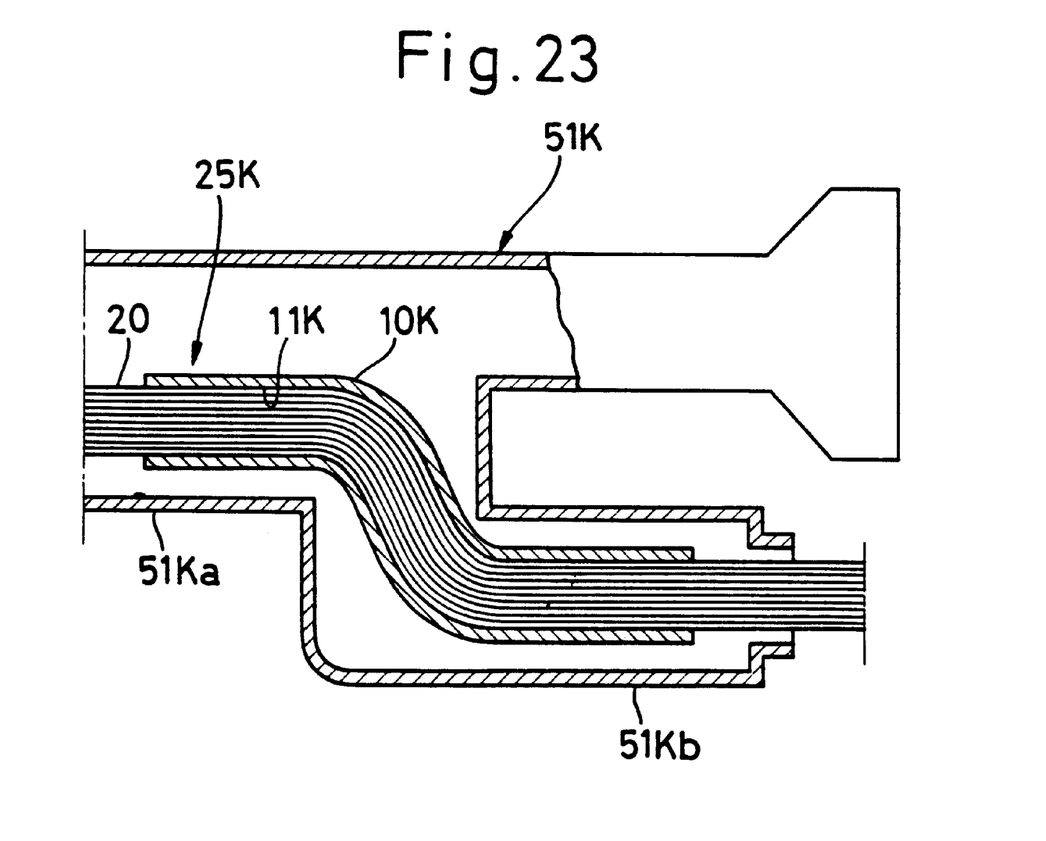
FIG. 23 is a longitudinal cross-sectional view of a body containing optical fibers united by the method of FIG. 22.

FIGS. 22 and 23 show a method of uniting optical fibers intermediate opposite ends thereof. As shown in FIG. 23, in its memorized shape, a tubular member 10K used in this embodiment has a circular cross-section, and has a generally S-shaped axis. As shown in FIG. 22, the tubular member 10K is processed in such a manner that it is larger in diameter and is curved along its axis more gently than its memorized shape. A number of optical fibers 20 are inserted through the tubular member 10K. At this time, the curvature or bending of the tubular member 10K in the axial direction is gentle, and besides the cross-sectional area of a reception space 11K is large, and therefore the insertion of the optical fibers 20 is easy. Then, the tubular member 10K is heated to be returned to its memorized shape, so that the tubular member 10K is reduced in diameter and is brought into the S-shaped, bent condition, thereby uniting the optical fibers 20 intermediate the opposite ends thereof. The opposite end portions of the optical fibers 20 are united in the manner as described above in any one of the above embodiments.

An optical fiber bundle 25K obtained by thus uniting the optical fibers 20 is incorporated into an endoscope. An intermediate portion of the optical fiber bundle 25K is received within a body 51K of the endoscope. The body 51K includes a base portion 51Ka, and a hollow projection 51Kb projected from the base portion 51Ka. The above tubular member 10K is received in the base portion 51Ka and the projection 51Kb. The optical fiber bundle 25K extended from the projection 51Kb is covered by a light guide cable. The optical fiber bundle 25K is protected by the tubular member 10K, and therefore is prevented from being damaged by movable portions in the body 51K.

Figure 24:
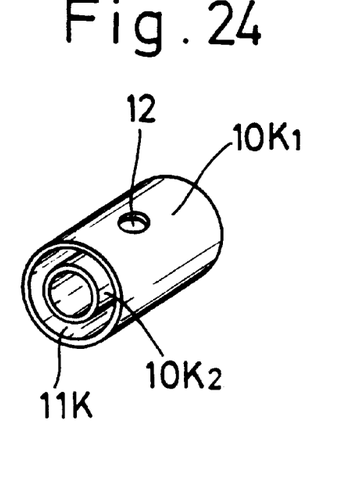
FIG. 24 is a perspective view of two tubular members used for uniting optical fibers.
Figure 25:
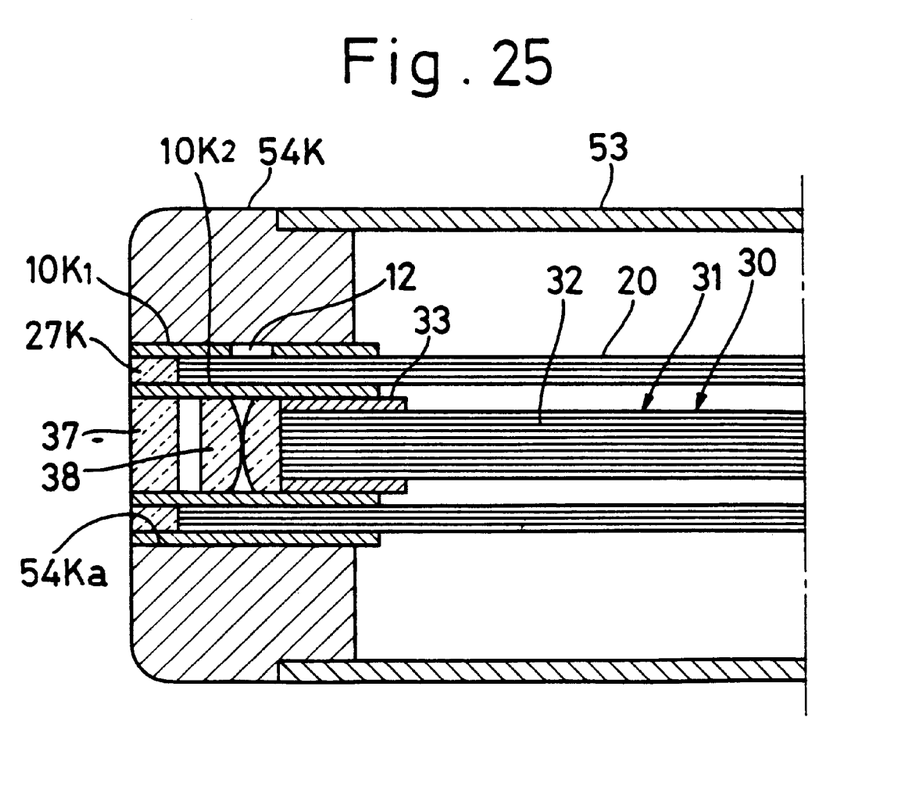
FIG. 25 is a longitudinal cross-sectional view showing a tip member containing the end portions of the optical fibers united by the use of the two tubular members of FIG. 24.

In the embodiment shown in FIGS. 24 and 25, there are used an outer tubular member $10K_1$ of a transverse circular cross-section and an inner tubular member $10K_2$ of a transverse circular cross-section smaller in diameter than the outer tubular member $10K_1$. The outer tubular member $10K_1$ is made of a shape memory alloy, and is processed in such a manner that it is larger in diameter than its memorized shape. The outer tubular member $10K_1$ has a through hole 12 for allowing the leakage of an adhesive. The inner tubular member $10K_2$ is received in the outer tubular member $10K_2$ to form a reception space 11K therebetween, and one end portions of optical fibers 20 are inserted into the reception space 11K. At this time, the front ends of the optical fibers 20 are spaced rearwardly from one ends of the tubular members $10K_1$ and $10K_2$. Then, the outer tubular member $10K_1$ is heated to be returned to its memorized shape having the smaller diameter, thereby uniting the optical fibers 20. Then, one end portion of an image transmission optical system 30 including an objective lens is inserted into and fixed to the inner tubular member $10K_2$, and an annular glass pane 27K serving as an illumination window is fitted between the front end portions of the tubular members $10K_1$ and $10K_2$. A tip assembly thus obtained is fitted in and fixed to a through hole 54Ka in a tip member 54K.

Figure 26:
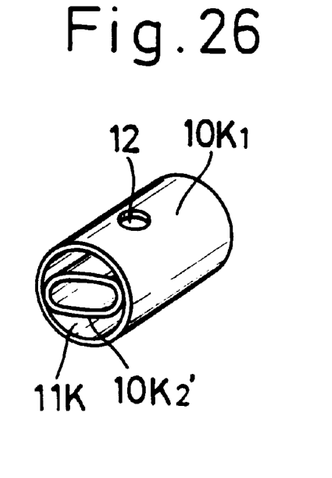
FIG. 26 is a perspective view of modified two tubular members similar to those of FIG. 24.

The inner tubular member $10K_2$ of FIG. 24 may be replaced by an inner tubular member $10K_2'$ of FIG. 26. Instead of the outer tubular member $10K_1$, the inner tubular member $10K_2$, $10K_2'$ may be made of a shape memory alloy. Alternatively, in addition to the outer tubular member $10K_1$, the inner tubular member $10K_2$, $10K_2'$ may be made of a shape memory alloy. In these cases, the inner tubular member $10K_2$, $10K_2'$ is processed in such a manner that it is smaller in diameter than its memorized shape, and when the inner tubular member is heated, it is returned to its memorized shape having the larger diameter, thereby reducing the cross-sectional area of the reception space 11K. Instead of the outer tubular member $10K_1$, the inner tubular member $10K_2$ may have an adhesive leakage through hole. Alternatively, in addition to the outer tubular member $10K_1$, the inner tubular member $10K_2$ may have an adhesive leakage through hole.

Figure 27:
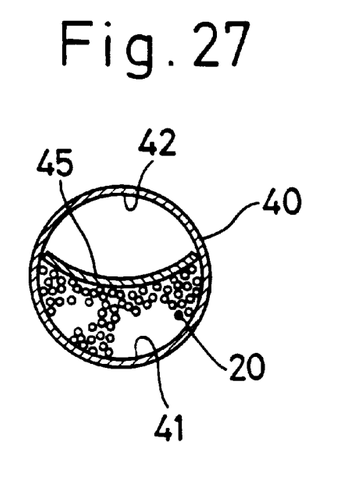
FIG. 27 is a transverse cross-sectional view of a tubular member and a partition member used in a further modified optical fiber uniting method, showing a condition in which optical fibers have not yet been united.
Figure 28:
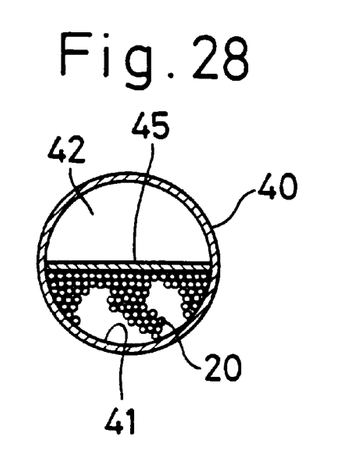
FIG. 28 is a transverse cross-sectional view showing a condition in which the optical fibers are united together by heating the partition plate of FIG. 27.
Figure 29:
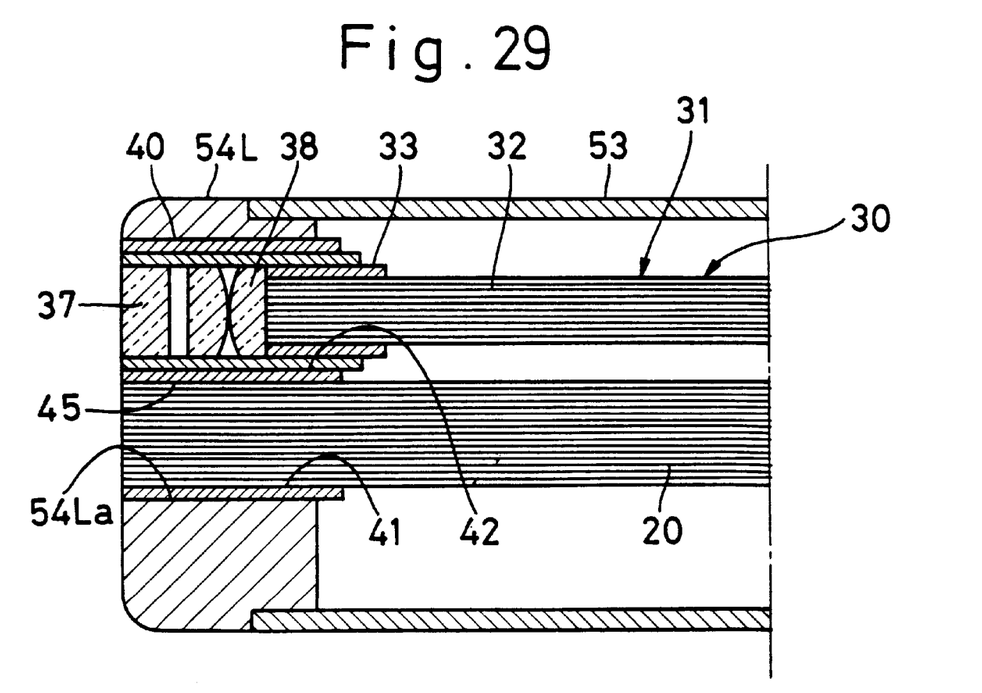
FIG. 29 is a longitudinal cross-sectional view of a tip member containing the end portions of the optical fibers united by the method of FIG. 28.

In the embodiment shown in FIGS. 27 to 29, there are used a tubular member 40 and a partition plate 45 of a shape memory alloy. As shown in FIG. 28, the partition plate 45 in its memorized shape is flat, and has a width equal to the inner diameter of the tubular member 40. The partition plate 45 is processed in such a manner that it is curved into an arcuate transverse cross-section at an ordinary temperature. The curved partition plate 45, when received into the tubular member 40, divides an internal space of the tubular member 40 into two sections, that is, a pair of reception spaces 41 and 42. One end portions of optical fibers 20 is inserted into the lower reception space 41 of a larger volume. Alternatively, the end portions of the optical fibers 20 are first inserted into the tubular member 40, and then the partition plate 45 is inserted into the tubular member 40 in such a manner that the partition plate 45 rests on the optical fibers 20 during the insertion.

Then, the partition plate 45 is heated to be returned to its memorized shape, that is, the flat shape. As a result, the partition plate 45 is disposed on the center of the tubular member 40, and the cross-sectional area of the reception space 41 is reduced, thereby uniting the end portions of the optical fibers 20. Preferably, the central portion of the partition plate 45 is prevented by a jig from upward movement when the partition plate 45 is to be heated.

Then, a front end portion of an image transmission optical system 30 is inserted into and fixed to the other reception space 42. A tip assembly thus obtained is fitted in and fixed to a through hole 54La in a tip member 54L.

The present invention is not limited to the above embodiments, and various modifications can be made. For example, the cross-sectional area of the reception space may be reduced by returning the tubular member from a transverse circular cross-section to a memorized, transverse non-circular cross-section by application of heat. Where there are used a pair of tubular members, and the inner tubular member is made of a shape memory alloy, the cross-sectional area of the reception space may be reduced by returning the inner tubular member from a non-circular cross-section to a memorized, circular cross-section by application of heat.

The united optical fibers may be used in the image transmission optical system of the endoscope. The united optical fibers may also be used in other devices than an endoscope.

What is claimed is:

1. A method of uniting a number of optical fibers comprising the steps of:

(a) processing a tubular member of a shape memory alloy with a reception space in such a manner that the cross-sectional area of said reception space is larger than that in a memorized shape of said tubular member;

(b) inserting the number of optical fibers into said tubular member; and (c) subsequently heating said tubular member to return the same to its memorized shape to reduce the cross-sectional area of said reception space, thereby uniting said optical fibers received in said tubular member, wherein said tubular member comprises a coil.

* * * * *